United States Patent [19]

Bream

[11] 4,045,572
[45] Aug. 30, 1977

[54] 3-AMINO-1-PHENYL-1H,5H,-BENZO-2,4-THIAZEPINES

[75] Inventor: John Bernard Bream, Bern, Switzerland

[73] Assignee: Sandoz Ltd., Basel, Switzerland

[21] Appl. No.: 690,210

[22] Filed: May 26, 1976

[30] Foreign Application Priority Data

| May 28, 1975 | United Kingdom | 23290/75 |
|---|---|---|
| May 28, 1975 | United Kingdom | 23291/75 |
| Jan. 14, 1976 | United Kingdom | 1909/76 |

[51] Int. Cl.² ........................................ C07D 281/02
[52] U.S. Cl. ................................. 424/275; 260/327 B
[58] Field of Search .................... 260/327 B; 424/275

[56] References Cited

PUBLICATIONS

Reinhoudt, Recl. Trav. Chim. Pays.-Bas 1973, 92(1), 20-32, (cited as Chem. Abs. 78; 136248e, 1973).

*Primary Examiner*—Cecilia M. S. Jaisle
*Attorney, Agent, or Firm*—Gerald D. Sharkin; Robert S. Honor; Thomas O. McGovern

[57] ABSTRACT

This invention provides new compounds of formula I,

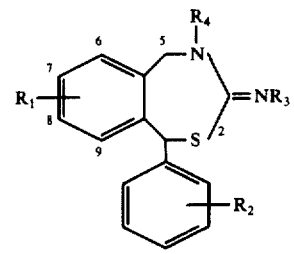

I wherein $R_1$ and $R_2$ are independently hydrogen, halogen, trifluoromethyl, lower alkoxy or lower alkyl, $R_3$ is hydrogen, lower alkyl, lower hydroxyalkyl, or phenylalkyl of 7 to 10 carbon atoms, wherein the phenyl ring is unsubstituted or mono-substituted, or independently di-substituted, by halogen, lower alkyl, lower alkoxy, amino, lower alkylamino or di(lower alkyl)amino, and $R_4$ is hydrogen, lower alkyl or lower hydroxyalkyl, useful as anti-arrhythmics and anti-depressants.

69 Claims, No Drawings

3-AMINO-1-PHENYL-1H,5H,-BENZO-2,4-THIAZE-PINES

The present invention reltes to benzo-3,4-thiazepines.

The present invention provides new compounds of formula I,

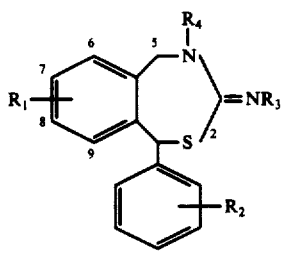

wherein
$R_1$ and $R_2$ are independently hydrogen, halogen, trifluoromethyl, lower alkoxy or lower alkyl,
$R_3$ is hydrogen, lower alkyl, lower hydroxyalkyl, or phenylalkyl of 7 to 10 carbon atons, wherein the phenyl ring is unsubstituted or mono-substituted, or independently di-substituted by halogen, lower alkyl, lower alkoxy, amino, lower alkylamino or di(lower alkyl)amino, and
$R_4$ is hydrogen, lower alkyl or lower hydroxyalkyl.

$R_1$ is preferably in the 7 or 8 position, especially the 8 position. $R_1$ is preferably hydrogen, or halogen.

$R_2$ is conveniently in the ortho or para position. $R_2$ is, however, preferably hydrogen.

$R_3$ is conveniently substituted or unsubstituted phenylalkyl. When the phenyl ring of $R_3$ is substituted it is preferably mono-substituted. When the phenyl ring is di-substituted, the substituents are preferably the same and are preferably other than amino. One substituent in the phenyl ring is preferably in the para position.

It will be appreciated that when $R_4$ is hydrogen, the compounds also exist in the following tautomeric form of formula Ia,

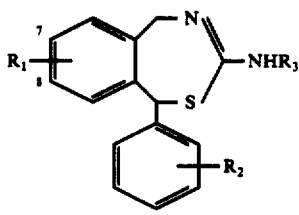

wherein $R_1$, $R_2$ and $R_3$ are as defined above.

Halogen is fluorine, bromine or preferaby chlorine.

"Lower alkyl, lower hydroxyalkyl or lower alkoxy" as used herein preferably refers to radicals of up to 4 carbon atoms, especially 1 or 2 carbon atoms. However, lower hydroxyalkyl especially refers to radicals containing 2 or 3 carbon atoms. Additionally, $R_3$ and $R_4$ when lower alkyl especially have 1 to 3 carbon atoms.

The present invention furthermore provides a process for the production of a compound of formula I as defined above which comprises intramolecularly cyclizing a compound of formula II,

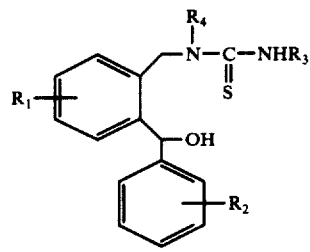

wherein $R_1$ to $R_4$ are as defined above.

The reaction may be carried out in conventional manner for such intramolecular cyclizations. For example, the reaction may be carried out in the presence of a strong acid, for example hydrochloric acid, trifluoroacetic acid, or benzenesulphonic acid. The reaction may be effected in the presence of water. Conveniently an organic solvent is used, e.g. glacial acetic acid, a lower alcohol such as ethanol, or preferably an aliphatic ketone such as acetone. A suitable temperature is from 20° to 150° C, preferably room temperature.

A compound of formula II, wherein $R_4$ is hydrogen, may be produced by reacting a compound of formula III,

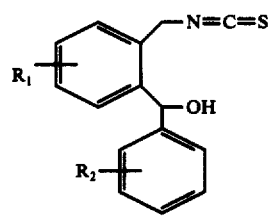

wherein $R_1$ and $R_2$ are as defined above, with an amine of formula $R_3NH_2$, wherein $R_3$ is as defined above, in conventional manner.

Alternatively a compound of formula IV,

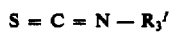

$$S = C = N - R_3'$$ 
IV wherein $R_3'$ is hydrogen, lower alkyl, phenylalkyl of 7 to 10 carbon atoms, wherein the phenyl ring is unsubstituted, or mono-substituted, or independently di-substituted, by halogen, lower alkyl, lower alkoxy, or di(lower alkyl) amino, may be reacted in conventional manner with a compound of formula V,

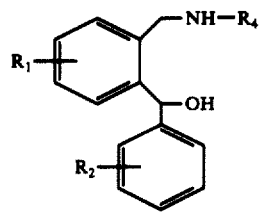

wherein $R_1$, $R_2$ and $R_4$ are as defined above, to produce the corresponding compound of formula II, wherein $R_3$ is $R_3'$ as defined above.

A compound of formula III, as defined above, may be produced by reacting in conventional manner carbon disulphide, ethyl chloroformate and a compound of formula V, wherein $R_4$ is hydrogen.

Insofar as the production of the starting materials is not particularly described, these compounds are known or may be produced and purified in accordance with known processes, or in a manner analogous to the processes described herein e.g. in the Examples where appropriate using suitable protecting groups.

The above mentioned compounds may be isolated and purified using conventional techniques. Free base forms of the compounds of formula I may be converted into acid addition salt forms in conventional manner and vice versa. A suitable salt is the hydrobromide or hydrochloride salt.

In the following examples all temperatures are uncorrected and are in degrees Centigrade.

Melting points refer to the hydrochloride form with decomposition unless stated otherwise, e.g.
1. no decomposition
2. hydrobromide salt
3. hydrochloride salt demi-hydrate.

EXAMPLE 1

8-Chloro-3-phenylethylamino-1-phenyl-1H,5H-benzo-2,4-thiazepine a. A solution of 1-(4-chloro-2-(α-hydroxybenzyl)-benzyl)-3-phenethyl-thiourea (17 g; 0.041 mole) in dry acetone (400 ml) and 85 ml saturated ethanolic hydrogen chloride was stirred at room temperature for 20 hours. The reaction mixture was filtered. The filtrate was evaporated to yield the title compound in hydrochloride form (M.Pt. 120° decomp.).

The starting material was obtained as follows:

b. 2-aminomethyl-5-chlorobenzhydrol (10 g; 0.04 mole) in 100 ml methanol and 2 ml triethylamine was treated dropwise with a solution of phenethyl isothiocyanate (8.6 g; 0.053 mole) in 25 ml of methanol. After 16 hours at room temperature the reaction mixture was evaporated and the residue was extracted with petroleum ether. The residual oil was recrystallized from diisopropyl ether to yield 1-(4-chloro-2-(α-hydroxybenzyl)benzyl)-3-phenethylthiourea as a white powder (M.Pt. 97° — 101°).

In analogous manner to that described in Example 1a the following compounds of formula I are produced wherein $R_4$ is hydrogen, and:

| Ex. No. | $R_1$ | $R_2$ | $R_3$ | M.Pt. |
|---|---|---|---|---|
| 2) | 8-Cl | H | CH$_3$ | 204–206° |
| 3) | H | H | CH$_3$ | 194–195° [1) |
| 4) | H | H | C$_2$H$_5$ | 156–160° |
| 5) | H | H | isoC$_3$H$_7$ | 197–199° |
| 6) | 8-Cl | H | C$_2$H$_5$ | 187–188° [1) |
| 7) | 8-Cl | H | isoC$_3$H$_7$ | 194–195° [1) |
| 8) | 7-Cl | H | CH$_3$ | 192–193° |
| 9) | H | H | [CH$_2$]$_2$— | 175–177° |
| 10) | 7-Cl | H | isoC$_3$H$_7$ | 166–169° [1)3) |
| 11) | H | H | [CH$_2$]$_2$——Cl | 172–174° [1) |
| 12) | H | H | [CH$_2$]$_2$——OCH$_3$ | 124–127° [1) |
| 13) | H | H | [CH$_2$]$_2$—\CH$_3$ | 171–174° [1) |
| 14) | H | H | [CH$_2$]$_2$——OCH$_3$, OCH$_3$ | 137–140° [1) |
| 15) | H | H | [CH$_2$]$_3$— | 175–178° |
| 16) | H | H | CH$_2$CH$_2$——NH$_2$ | |
| 17) | H | H | CH$_2$CH$_2$——N(CH$_3$)$_2$ | |
| 18) | 7-Cl | H | CH$_2$CH$_2$——Cl | |
| 19) | H | H | CH$_2$CH$_2$——Cl, Cl | |
| 20) | 7-Cl | H | CH$_2$—CH$_2$—\CH$_3$ | |
| 21) | 7-Cl | H | CH$_2$—CH$_2$——OCH$_3$ | |

-continued

| Ex. No. | R₁ | R₂ | R₃ | M.Pt. |
|---|---|---|---|---|
| 22) | H | H | CH₂CH₂—(2,6-dichlorophenyl) | |
| 23) | H | 4'-Cl | CH₂CH₂—phenyl | |
| 24) | 8-Cl | H | CH₂CH₂CH₂—phenyl | |
| 25) | H | 4'-Cl | CH₂CH₂CH₂—phenyl | |
| 26) | 7-CH₃ | H | C₂H₅ | |
| 27) | 8-CH₃ | H | C₂H₅ | |
| 28) | 7-CH₃ | H | CH₂.CH₂—phenyl | |
| 29) | 8-CH₃ | H | CH₂.CH₂—phenyl | |
| 30) | H | H | H | |
| 31) | 8-Cl | H | H | |
| 32) | 8-CH₃ | H | CH₃ | |
| 33) | H | 2'-Cl | CH₃ | |
| 34) | H | 4'-CH₃ | CH₃ | |
| 35) | 7-Cl | H | C₂H₅ | |
| 36) | H | H | CH₂—phenyl | |
| 37) | H | H | [CH₂]₂OH | |
| 38) | H | H | [CH₂]₃OH | |
| 39) | 7-Cl | H | CH₂—CH₂—(2,3-dimethoxyphenyl) | |
| 40) | 7-Cl | H | CH₂—CH₂—CH₂—phenyl | |
| 41) | 8-Cl | H | CH₂—CH₂—phenyl | |

In analogous manner to Example 1 the following compounds of formula Ia are prepared, wherein:

| Ex. No. | R₁ | R₂ | R₃ | R₄ | M.Pt. |
|---|---|---|---|---|---|
| 42) | H | H | isoC₃H₇ | isoC₃H₇ | 226–227° |
| 43) | H | H | isoC₃H₇ | CH₃ | 226–227° |
| 44) | 8-Cl | H | CH₃ | CH₃ | 140–145° |
| 45) | H | H | CH₃ | isoC₃H₇ | 165–166°³⁾ |
| 46) | 7-Cl | H | CH₃ | CH₃ | 196–198° |
| 47) | H | H | CH₃ | CH₃ | 189–190° |
| 48) | H | H | C₂H₅ | C₂H₅ | 182–184° |
| 49) | H | H | n-C₃H₇ | n-C₃H₇ | 213–216°¹⁾²⁾ |
| 50) | 8-Cl | H | n-C₃H₇ | n-C₃H₇ | 133–135°¹⁾³⁾ |
| 51) | H | H | CH₂.CH₂—phenyl | CH₃ | 191–195°¹⁾²⁾ |
| 52) | H | H | CH₃ | CH₃ | |
| 53) | 8-CH₃ | H | CH₃ | CH₃ | |
| 54) | H | 2'-Cl | CH₃ | CH₃ | |
| 55) | H | 4'-CH₃ | CH₃ | CH₃ | |
| 56) | H | H | CH₃ | [CH₂]₂OH | |
| 57) | H | H | [CH₂]₂OH | CH₃ | |
| 58) | H | H | C₂H₅ | CH₃ | |
| 59) | 7-Cl | H | C₂H₅ | CH₃ | |
| 60) | 8-Cl | H | C₂H₅ | CH₃ | |
| 61) | H | H | [CH₂]₂OH | CH₃ | |
| 62) | 7-Cl | H | [CH₂]₂OH | CH₃ | |
| 63) | 8-Cl | H | [CH₂]₂OH | CH₃ | |

EXAMPLE 64

1-(2-(α-hydroxybenzyl)benzyl)-3-phenethylthiourea (starting material for Example 9)

a. A solution of 1 g of 2-aminomethylbenzhydrol hydrochloride in 4 ml of water is added dropwise to a mixture of 0.32 g of sodium hydroxide in 2 ml water and 0.25 ml carbon disulphide cooled in ice. The mixture is maintained at room temperature for 30 minutes and then on a steam bath for 30 minutes. 0.28 ml of ethyl chloroformate is added to the cooled reaction mixture, which is stirred at room temperature overnight. The solution is worked up in conventional manner to give 1-(2-(α-hydroxybenzyl)benzyl)-isothiocyanate as an oil.

b. 500 mg of 1-(2-(α-hydroxybenzyl)benzyl)-isothiocyanate and 240 mg of phenylethyl-amine in 10 ml of benzene are maintained for 4.5 days at room temperature, and worked up in conventional manner to yield the title compound in free base form; M.Pt. 117° - 119°.

The compounds of formula I exhibit pharmacological activity. In particular, the compounds of formula I exhibit anti-arrhythmic activity as indicated in standard tests, for example (i) by an anti-arrhythmic effect in the chloroform arrhythmia test in the mouse according to the method of J. W. Lawson [J. Pharmac. exp. Ther., 160, 22-31 (1968)] on administration i.p. of 5 to 50 mg/kg animal body weight of the compounds, and (ii) by a prolongation of the functional refractory period of the isolated albino guinea pig left atria according to the method of N. Reuter, E. Haag and U. Haller [Arch. Pharmac., 268, 323-333, (1971)] using a bath concentration of 1 to 25 μM of the compounds.

The compounds are therefore useful as antiarrhythmic agents for the treatment of heart rhythm disorders.

For the above mentioned use the dosage will, of course, vary depending on the compound employed, mode of administration and therapy desired. However, in general, satisfactory results are obtained when administered at a daily dosage of from 0.01 mg to about 50 mg per kg animal body weight, conveniently given in divided doses 2 to 4 times a day or in sustained release form. For the larger mammal, the total daily dosage is in the range from about 1 to about 50 mg, and dosage forms suitable for oral administration comprise from about 0.2 mg to about 25 mg of the compounds admixed with a solid or liquid pharmaceutical carrier or diluent.

The compounds of formula I additionally exhibit anti-depressant activity as indicated in standard tests, for example, the tetrabenazine antagonism test in the mouse on administration i.p. of form 1 to 50 mg/kg animal body weight of the compounds.

The compounds are further useful for use as antidepressant agents for the treatment of exogeneous and endogeneous depressions.

For the above mentioned use the dosage will, of course, vary depending on the compound employed, mode of administration and therapy desired. However, in general, satisfactory results are obtained when administered at a daily dosage of from 0.01 mg to about 50 mg per kg animal body weight, conveniently given in divided doses 2 to 4 times a day or in sustained release form. For the larger mammal, the total daily dosage is in the range from about 1 to about 100 mg, and dosage forms suitable for oral administration comprise from about 0.2 mg to about 50 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. The present invention also provides a pharmacological composition comprising a compound of formula I, in free base form or in pharmaceutically acceptable acid addition salt form, in association with a pharmaceutical carrier or diluent. Such compositions may be in the form of, for example, a solution or a table.

In one group of compounds $R_1$ and $R_2$ are independently hydrogen, halogen or lower alkyl and $R_3$ is lower alkyl or hydroxyalkyl. In a sub-group $R_4$ is hydrogen. In another sub-group $R_4$ is lower alkyl or hydroxyalkyl.

In a preferred group of compounds $R_3$ is $R_3'$ as defined above, and especially $R_4$ is hydrogen.

The Example 1 compound is the preferred compound.

I claim:

1. A compound of formula I,

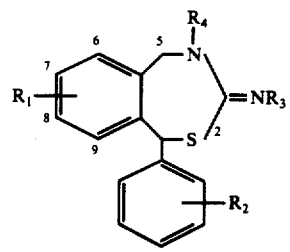

wherein
$R_1$ and $R_2$ are independently hydrogen, halogen, trifluoromethyl, lower alkoxy or lower alkyl,
$R_3$ is hydrogen, lower alkyl, lower hydroxyalkyl, or phenylalkyl of 7 to 10 carbon atoms, wherein the phenyl ring is unsubstituted or mono-substituted, or independently di-substituted, by halogen, lower alkyl, lower alkoxy, amino, lower alkylamino or di(lower alkyl)amino, and
$R_4$ is hydrogen,
in free base form or in pharmaceutically acceptable acid addition salt form thereof.

2. A pharmaceutical composition useful in treating depression or heart rhythm disorder comprising a therapeutically effective amount of a compound of claim 1 in association with a pharmaceutical carrier or diluent.

3. A method of treating depressions in animals which comprises administering a therapeutically effective amount of a compound of claim 1 to an animal in need of such treatment.

4. A method of treating heart rhythm disorders in animals which comprises administering a therapeutically effective amount of a compound of claim 1 to an animal in need of such treatment.

5. A compound of claim 1, wherein $R_1$ and $R_2$ independently are hydrogen, lower alkyl or halogen, and $R_3$ is lower alkyl or hydroxyalkyl.

6. A compound of claim 1 which is 8-chloro-3-phenylethylamino-1-phenyl-1H,5H-benzo-2,4-thiazepine.

7. A compound of the formula

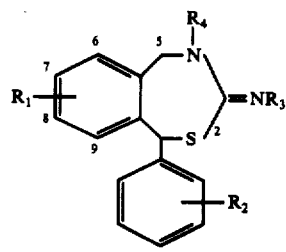

wherein
$R_1$ and $R_2$ are independently hydrogen, halogen, trifluoromethyl, lower alkoxy or lower alkyl,
$R_3$ is hydrogen, lower alkyl, or phenylalkyl of 7 to 10 carbon atoms, wherein the phenyl ring is unsubstituted or mono-substituted, or independently di-substituted, by halogen, lower alkyl, lower alkoxy, or di (lower alkyl)amino, and $R_4$ is hydrogen, lower alkyl or lower hydroxyalkyl, in free base form or in pharmaceutically acceptable acid addition salt form thereof.

8. A pharmaceutical composition useful in treating depression or heart rhythm disorder comprising a therapeutically effective amount of a compound of claim 7 in association with a pharmaceutical carrier or diluent.

9. A method of treating depressions in animals which comprises administering a therapeutically effective amount of a compound of claim 7 to an animal in need of such treatment.

10. A method of treating heart rhythm disorders in animals which comprises administering a therapeutically effective amount of a compound of claim 7 to an animal in need of such treatment.

11. A compound of claim 7, wherein $R_4$ is hydrogen.

12. A compound of claim 7, wherein $R_4$ is lower alkyl or lower hydroxyalkyl.

13. A compound of claim 1, wherein $R_1$, $R_2$ and $R_3$ respectively are 8-Cl, H and $CH_3$.

14. A compound of claim 1, wherein $R_1$, $R_2$ and $R_3$ respectively are H, H, and $CH_3$.

15. A compound of claim 1, wherein $R_1$, $R_2$ and $R_3$ respectively are H, H and $C_2H_5$.

16. A compound of claim 1, wherein $R_1$, $R_2$ and $R_3$ respectively are H, H and iso$C_3H_7$.

17. A compound of claim 1, wherein $R_1$, $R_2$ and $R_3$ respectively are 8-Cl, H and $C_2H_5$.

18. A compound of claim 1, wherein $R_1$, $R_2$ and $R_3$ respectively are 8-Cl, H and iso$C_3H_7$.

19. A compound of claim 1, wherein $R_1$, $R_2$ and $R_3$ respectively are 7-Cl, H and $CH_3$.

20. A compound of claim 1, wherein $R_1$, $R_2$ and $R_3$ respectively are H, H and

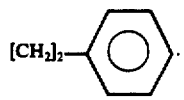

21. A compound of claim 1, wherein $R_1$, $R_2$ and $R_3$ respectively are 7-Cl, H and iso$C_3H_7$.

22. A compound of claim 1, wherein $R_1$, $R_2$ and $R_3$ respectively are H, H and

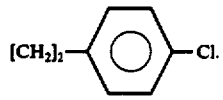

23. A compound of claim 1, wherein $R_1$, $R_2$ and $R_3$ respectively are H, H and

24. A compound of claim 1, wherein $R_1$, $R_2$ and $R_3$ respectively are H, H and

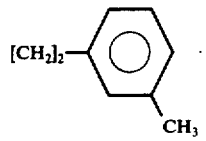

25. A compound of claim 1, wherein $R_1$, $R_2$ and $R_3$ respectively are H, H and

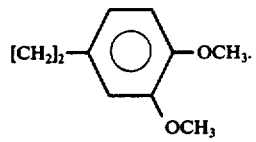

26. A compound of claim 1, wherein $R_1$, $R_2$ and $R_3$ respectively are H, H and

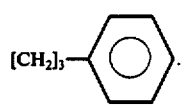

27. A compound of claim 1, wherein $R_1$, $R_2$ and $R_3$ respectively are H, H and

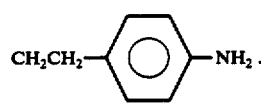

28. A compound of claim 1, wherein $R_1$, $R_2$ and $R_3$ respectively are H, H and

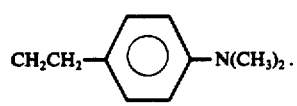

29. A compound of claim 1, wherein $R_1$, $R_2$ and $R_3$ respectively are 7-Cl, H and

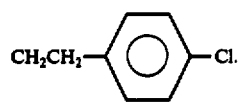

30. A compound of claim 1, wherein $R_1$, $R_2$ and $R_3$ respectively are H, H and

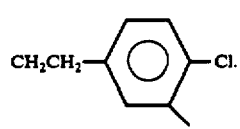

31. A compound of claim 1, wherein $R_1$, $R_2$ and $R_3$ respectively are 7-Cl, H and

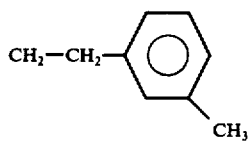

32. A compound of claim 1, wherein $R_1$, $R_2$ and $R_3$ respectively are 7-Cl, H and

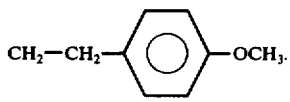

33. A compound of claim 1, wherein $R_1$, $R_2$ and $R_3$ respectively are H, H and

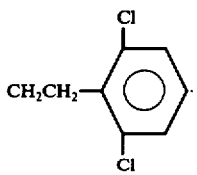

34. A compound of claim 1, wherein $R_1$, $R_2$ and $R_3$ respectively are H, 4'-Cl and

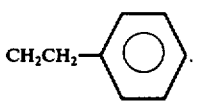

35. A compound of claim 1, wherein $R_1$, $R_2$ and $R_3$ respectively are 8-Cl, H and

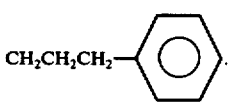

36. A compound of claim 1, wherein $R_1$, $R_2$ and $R_3$ respectively are H, 4'-Cl and

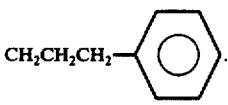

37. A compound of claim 1, wherein $R_1$, $R_2$ and $R_3$ respectively are 7-CH$_3$, H and C$_2$H$_5$.

38. A compound of claim 1, wherein $R_1$, $R_2$ and $R_3$ respectively are 8-CH$_3$, H and C$_2$H$_5$.

39. A compound of claim 1, wherein $R_1$, $R_2$ and $R_3$ respectively are 7-CH$_3$, H and

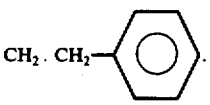

40. A compound of claim 1, wherein $R_1$, $R_2$ and $R_3$ respectively are 8-CH$_3$, H and

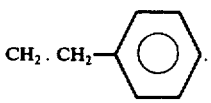

41. A compound of claim 1, wherein $R_1$, $R_2$ and $R_3$ respectively are H, H and H.

42. A compound of claim 1, wherein $R_1$, $R_2$ and $R_3$ respectively are 8-Cl, H and H.

43. A compound of claim 1, wherein $R_1$, $R_2$ and $R_3$ respectively are 8-CH$_3$, H and CH$_3$.

44. A compound of claim 1, wherein $R_1$, $R_2$ and $R_3$ respectively are H, 2'-Cl and CH$_3$.

45. A compound of claim 1, wherein $R_1$, $R_2$ and $R_3$ respectively are H, 4'-CH$_3$ and CH$_3$.

46. A compound of claim 1, wherein $R_1$, $R_2$ and $R_3$ respectively are 7-Cl, H and C$_2$H$_5$.

47. A compound of claim 1, wherein $R_1$, $R_2$ and $R_3$ respectively are H, H and

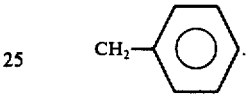

48. A compound of claim 1, wherein $R_1$, $R_2$ and $R_3$ respectively are H, H and [CH$_2$]$_2$OH.

49. A compound of claim 1, wherein $R_1$, $R_2$ and $R_3$ respectively are H, H and [CH$_2$]$_3$OH.

50. A compound of claim 1, wherein $R_1$, $R_2$ and $R_3$ respectively are 7-Cl, H and

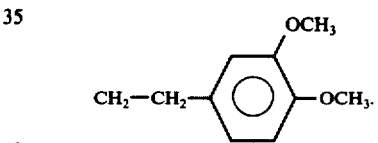

51. A compound of claim 1, wherein $R_1$, $R_2$ and $R_3$ respectively are 7-Cl, H and

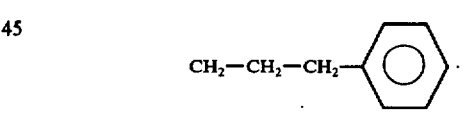

52. A compound of claim 1, wherein $R_1$, $R_2$ and $R_3$ respectively are 8-Cl, H and

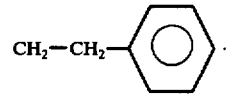

53. A compound of claim 7, wherein $R_1$, $R_2$, $R_3$ and $R_4$ respectively are H, H, isoC$_3$H$_{67}$ and isoC$_3$H$_7$.

54. A compound of claim 7, wherein $R_1$, $R_2$, $R_3$ and $R_4$ respectively are H, H, isoC$_3$H$_7$ and CH$_3$.

55. A compound of claim 7, wherein $R_1$, $R_2$, $R_3$ and $R_4$ respectively are 8-Cl, H, CH$_3$ and CH$_3$.

56. A compound of claim 7, wherein $R_1$, $R_2$, $R_3$ and $R_4$ respectively are H, H, CH$_3$ and isoC$_3$H$_7$.

57. A compound of claim 7, wherein $R_1$, $R_2$, $R_3$ and $R_4$ respectively are 7-Cl, H, CH$_3$ and CH$_3$.

58. A compound of claim 7, wherein $R_1$, $R_2$, $R_3$ and $R_4$ respectively are H, H, $CH_3$ and $CH_3$.

59. A compound of claim 7, wherein $R_1$, $R_2$, $R_3$ and $R_4$ respectively are H, H, $C_2H_5$ and $C_2H_5$.

60. A compound of claim 7, wherein $R_1$, $R_2$, $R_3$ and $R_4$ respectively are H, H, n-$C_3H_7$ and n-$C_3H_7$.

61. A compound of claim 7, wherein $R_1$, $R_2$, $R_3$ and $R_4$ respectively ae 8-Cl, H, n-$C_3H_7$ and n-$C_3H_7$.

62. A compound of claim 7, wherein $R_1$, $R_2$, $R_3$ and $R_4$ respectively are H, H,

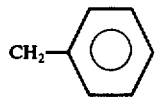

and $CH_3$.

63. A compound of claim 7, wherein $R_1$, $R_2$, $R_3$ and $R_4$ respectively are 8-$CH_3$, H, $CH_3$, and $CH_3$.

64. A compound of claim 7, wherein $R_1$, $R_2$, $R_3$ and $R_4$ respectively are H, 2'-Cl, $CH_3$ and $CH_3$.

65. A compound of claim 7, wherein $R_1$, $R_2$, $R_3$ and $R_4$ respectively are H, 4'-$CH_3$, $CH_3$ and $CH_3$.

66. A compound of claim 7, wherein $R_1$, $R_2$, $R_3$ and $R_4$ respectively are H, H, $CH_3$ and $[CH_2]_2OH$.

67. A compound of claim 7, wherein $R_1$, $R_2$, $R_3$ and $R_4$ respectively are H, H, $C_2H_5$ and $CH_3$.

68. A compound of claim 7, wherein $R_1$, $R_2$, $R_3$ and $R_4$ respectively are 7-Cl, H, $C_2H_5$ and $CH_3$.

69. A compound of claim 7, wherein $R_1$, $R_2$, $R_3$ and $R_4$ respectively are 8-Cl, H, $C_2H_5$ and $CH_3$.

* * * * *